Figure 1:
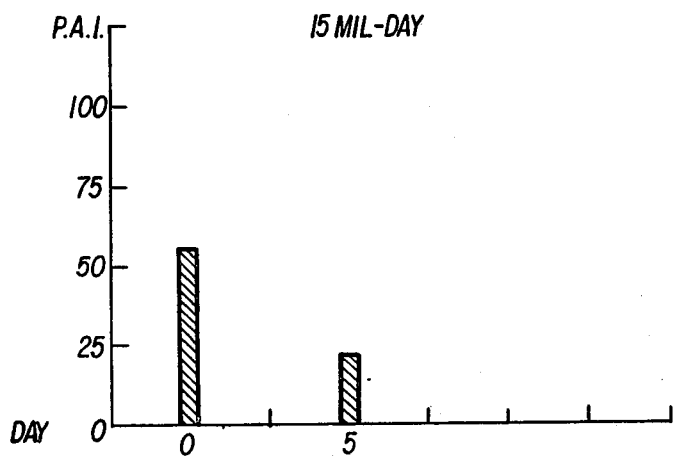

United States Patent [19]

Martin

[11] 4,061,738
[45] Dec. 6, 1977

[54] PROCESS FOR REDUCING PLATELET ADHESIVENESS

[76] Inventor: Wayne Martin, 1222 Pelham Drive, Fort Wayne, Ind. 46825

[21] Appl. No.: 644,812

[22] Filed: Dec. 29, 1975

Related U.S. Application Data

[63] Continuation-in-part of Ser. No. 476,337, June 4, 1974, abandoned, which is a continuation of Ser. No. 249,741, May 2, 1972, abandoned, which is a continuation of Ser. No. 98,160, Dec. 14, 1970, abandoned, which is a continuation of Ser. No. 626,101, March 27, 1967, abandoned.

[51] Int. Cl.² .............................................. A61K 35/78
[52] U.S. Cl. ..................................................... 424/195
[58] Field of Search ................................ 424/195, 199

[56] References Cited

U.S. PATENT DOCUMENTS 3,163,545  12/1964  Martin ..................................... 99/192

Primary Examiner—Stanley J. Friedman
Attorney, Agent, or Firm—Stevens, Davis, Miller & Mosher

[57] ABSTRACT

A process for reducing platelet adhesiveness in flowing human blood by orally administering to humans an effective amount of an enriched, edible flaxseed oil. The oil is obtained by pressing flaxseeds under controlled conditions and adding thereto 3% by weight of flax phosphatides, 3% by weight of soy phosphatides and a small amount of mixed grain and soya tocopherols.

5 Claims, 5 Drawing Figures

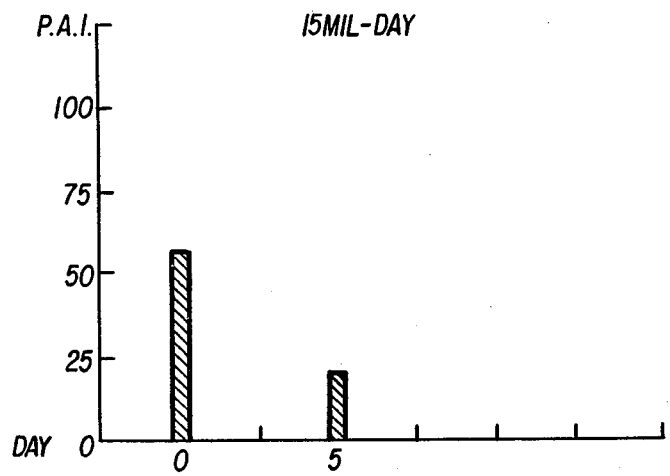
FIG. 4
FIG. 5
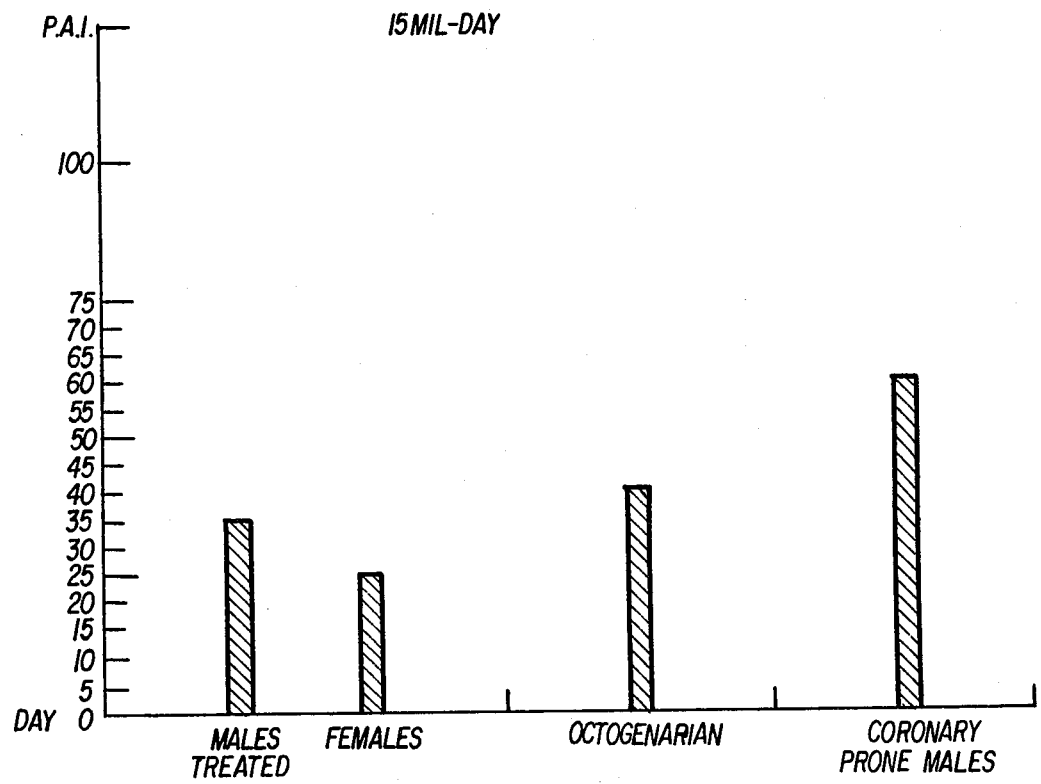

PROCESS FOR REDUCING PLATELET ADHESIVENESS

This application is a continuation-in-part of application Ser. No. 476,337, filed June 4, 1974, now abandoned which is a continuation of application Ser. No. 249,741, filed May 2, 1972, now abandoned, which is a continuation of application Ser. No. 98,160, filed Dec. 14, 1970, now abandoned, which in turn is a continuation of application Ser. No. 626,101, filed Mar. 27, 1967, now abandoned.

This discovery relates to a method of reducing platelet adhesiveness and therefore the aggregation of platelets in flowing blood within human subjects. Aggregation of platelets is commonly accepted as the first stage of intravascular thrombosis in flowing blood and is the type of thrombosis which occurs in coronary thrombosis. By reducing platelet adhesiveness, I propose to inhibit the occurrence of coronary thrombosis.

For the past decade medical opinion has held that coronary thrombosis is related to a disease state referred to as atherosclerosis. In atherosclerosis, atheroma, a yellow wax-like material containing fatty acids in diet along with cholesterol, is deposited in the arteries under the capillary membrane, the endothelium. In time the endothelium will thicken and become fragile. As long as the endothelium remains intact, blood is unlikely to clot at the site of atheroma. Eventually, however, in the intrinsic blood system the endothelium over a plaque of atheroma will ulcerate or break, or become damaged and disappear and a thrombus is likely to form at that location. Quite often the result is death.

It follows that if these described widespread and deeply held beliefs had validity the degree of atheroma would be greater in parts of the world where the degree of thrombosis is greater. As inhabitants of Japan are predisposed to suffer only about one-tenth the number of fatalities from thrombosis as compared to people in the United States (on a unit basis), it should follow that atheroma among people in Japan is only one-tenth as prevalent as in the United States. The evidence shows no such correlation. Gore (*American Journal of Clinical Nutrition*, Jan. 1959, vol. 7, page 50) did a pathological study on the degree of atheroma both in the United States and Japan on a comparative basis. What was found in both nations is that the degree of atheroma increased with age until the seventh decade of life at which time it became most severe in individuals of both nations. There was essentially no difference in the degree of atheroma, age group for age group, in the two nations. Confronted by a situation in which inhabitants of the two nations experience the same degree of atheroma, there is a difference of a factor of ten with respect to thrombosis. This undisputed evidence clearly indicates the presence of some unappreciated factor causing thrombosis.

In Sweden during World War II drastic food rationing resulted from wartime conditions in late 1939. From then until mid-1941 there was a substantial drop in coronary thrombosis. After food shipment limitations into Sweden were lifted, the death rate from coronary thrombosis began to increase and is still increasing. (Malmros, Acto Med. Scandinav., Suppl. 246; 137 1950). As atheroma takes a lifetime to form and is never known to retrogress in humans, such change as occurred in Sweden in a brief two-year period could have had no effect on the degree of atheroma. Thus Malmros's statistics in Sweden confirmed the presence of another factor as suggested by Gore's work and further indicated that this "other factor" was fact acting.

Kagan (*Health Horizon*, Summer 1959) has pointed out that coronary thrombosis among middle aged males in England in 1959 was three times more prevalent than it was prior to 1939 and was virtually unknown until after 1918, and is ever increasing. Sinclair (*Health Horizon*, Summer 1959) pointed out that a change in dietary fat processing has probably altered clot formation and hence incidence of thrombosis. He indicated that death due to clots in the coronary arteries is increasing at the same rate as death due to clots in the lung. In his study of the effects of stress and atheroma, he found that the drop in deaths due to thrombosis in the Scandinavian nations during World War II occurred at a time when dietary fats were altered on a national basis; that this fast change could not be accounted for by a change in degree of atheroma because if that were altered at all, it would have been slowly; and that in Norway the drop in deaths from thrombosis occurred at a time when the stress of life was at a maximum, due to living under wartime conditions. Hence he presumed the presence of a fast acting factor not involved with either atheroma or stress and having a direct effect on thrombosis. In 1959 Shaper and Jones at Makerere College in Kampala, Uganda, reported that the negroes in Kampala had no incidence of death from coronary thrombosis (Lancet, Oct. 10, 1959, page 534). As a follow-up to this report O'Neil, in a study in pathology, found that while negroes in Kampala were free from death caused by thrombosis, negroes of the same age bracket in the United States had relatively the same death rate from thrombosis as whites of the same age group in the United States (O'Neil, *American Journal of Cardiology*, January 1960). O'Neil further suggested that this difference in death incidence from thrombosis was due to a dietary hematologic factor present in the diet of the Kampala negroes and either absent or present in too little quantity in the diet of negroes in the United States. He further suggests that a dietary alteration, by altering this hematologic factor, could thus alter the pattern of death from thrombosis.

In 1939, it was believed that blood clots whether in open wounds or intravascular such as in coronary thrombosis were triggered in the classic four factor process as follows: thromboplasten + $Ca^{++}$ (ion) + prothrombin > thrombin; and, thrombin + fibrinogen > fibrin. Fibrin is the solid threadlike material of the clot. Owren in Norway, working during wartime conditions, found that with open wounds, other factors were involved in triggering clot formation, especially a factor VII. This led to the discovery that dicoumarin derivatives found in hay will prevent the body from making factor VII. It explained why these derivatives had been used as anticoagulants and this led to the basis of use as rat poison, since if used in excess will cause death from internal hemorraging. For the past twenty years dicoumarin derivatives have, to a limited degree, been used in post thrombosis cases for humans in the belief that factor VII is involved in intravascular thrombosis and hence moderate suppression of factor VII will tend to prevent subsequent episodes of thrombosis. Recent statistical surveys have thrown into question the value of the use of such anticoagulant therapy (*Drug Trade News*, Nov. 7, 1966).

By 1948 it was beginning to be understood that there was more involved in a blood clot than the formation of a red fibrin thrombus.

In 1948 MacFarlane at Oxford pointed out that before a red fibrin clot can form, first a platelet clot must form. Paul Owren of Norway later elaborated on the formation of a white platelet clot or thrombus as we will presently note, however as of 1948 MacFarlane noted that platelets in the blood have a variable degree of stickiness and that before a red thrombus can form a white blood clot made up of sticky platelets must form and then and only then can the more massive red thrombus form on top of it.

In 1948, this was looked upon by many hematologists as a radical concept of little value.

MacFarlane points out that factor VII apparently is involved only where there is damaged tissue such as in open wounds and that conversely it is probably not involved in intrinsic coagulation as in coronary thrombosis (Biochemical Disorders in Human Diseases, Thompson and King, page 131). Best (Journal of Clinical Pathology, Vol. I, 1947–1948, page 138) has shown that heparin prevents platelet aggregation and thrombosis formation on intimal surfaces and is active and nontoxic in vivo. However, heparin while rapid in effect is of very short duration, and can only be used in hospitals where it can be given by continuous intravenous injection or by four or more intravenous injections daily.

By 1965 Owren and most of the research hematologists in the world have now agreed that a red thrombus never forms without sticky platelets having first formed a white or platelet thrombus. This and more about the role of platelets in blood clotting Owren reported in 1965 (Annals of Internal Medicine, Vol. 63, August 1965, page 167). In this he pointed out that susceptibility to aggregation of platelets, which in turn leads to thrombosis, can be measured by a platelet adhesiveness index "PAI". He has demonstrated as has McDonald (The Lancet, May 30, 1959, page 1115) that subjects with various phases of ischaemic heart disease all have elevated PAI as compared to normal subjects. My own research has indicated that whereas young females 20–28 who are not prone to coronary thrombosis have a PAI of about 25; coronary prone males 50–70 have an average PAI of 50–60. The present invention teaches a means of reducing platelet adhesiveness index, this being the factor of reducing coronary thrombosis. Owren has confirmed that the hematologic factor referred to by O'Neil in his Kampala study is PAI or a dietary factor which regulates PAI.

Owren points out that as the endothelium over a plaque of atheroma becomes damaged, "platelets start within seconds to adhere to the endothelial cells or if these have been destroyed and removed, to tissue fibers, particularly to collagen fibers that become exposed to the blood stream. New platelets start to adhere to those already fixed and to each other, forming a loose platelet thrombus. These are easily disrupted and carried away by the blood stream but new aggregates are steadily formed. This is the stage of reversible platelet aggregation".

"After some minutes morphological changes are observed in the platelets. The loose granular platelet clumps fuses into a structural mass - - - . The white platelet thrombus thereby becomes strengthened and resistant to the blood streams". (Owren, loc. cit.)

Owren points out that the formation of loose platelet thrombi cannot be prevented by either heparin or by oral anticoagulants, that white thrombus formation cannot be prevented by anticoagulants whereas the later formation of red thrombus may so be prevented. White thrombi alone may occlude stenotic coronary arteries and for this reason it is important to find some means to prevent the formation of white thrombus which may be in itself fatal or which will in turn lead to the formation of the fatal red thrombus. Owren pointed out that in Norway during a wartime period there was drastic food rationing which coincided with a decided drop in death from thrombosis. During this period the milling of wheat was forbidden, hence bread was whole wheat and contained all the wheat germ oil in the wheat grain. The wheat germ oil is 6% linolenic acid and Owren pointed out that during this period linolenic acid content in fact was 1.6% of total dietary fat. Now in Norway death from thrombosis has increased two-fold while linolenic acid content of dietary fat has decreased to about 0.7% of total dietary fat. He therefore presumed that the lowering in death from thrombosis during the German occupation in Norway was due to a lowering of PAI, due to the high content of linolenic acid in the Norwegian diet of that time.

As flaxseed oil contains about 50% linolenic acid, it was presumed that with an average individual an addition of 15 ml per day of flaxseed oil to diet will bring linolenic acid content to about 3% of total dietary fat. Subjects with PAI, range 50–70, were given 15 ml of refined flaxseed oil per day and in three days time PAI was reduced to a 30–40 level. These results were published and great attention was paid to these findings, for it was felt that this would open the way to safe dietary anticoagulant prevention and a cure for thrombosis. Other researchers shortly thereafter reported no reduction in PAI after feeding subject refined flaxseed oil. In October 1965, Owren repudiated his original report and reported no reduction in PAI with flaxseed oil feeding. Evans and Irving (Lancet, Aug. 13, 1966) reported no reduction in PAI with corn oil, flaxseed oil and dicoumarin.

In Kampala, where negroes have no thrombosis, a principal dietary grain is millet seed eaten as a whole grain. Since millet seed oil contains 6% linolenic acid, it is probable that the diet of these negroes contains over 3% linolenic acid.

When the whole grain is eaten, all substances in the grain oil are eaten including the phosphatides. In the processing of vegetable oils the first step is to degum the oil in which case most the phosphatides are removed. In my U.S. Pat. No. 3,163,545, I have found that these phosphatides which are removed in refining are beneficial and must be left in the oil. In the formula set forth as a specific example, I not only leave the phosphatides that were in the whole grain in the oil, but I use crude phosphatides which are removed from other oil as an additive which is blended to enrich my oil.

SPECIFIC EXAMPLE

In the processing of flaxseed oil manufactured in accordance with U.S. Pat. No. 3,163,545, half the oil is removed by pressing. As discussed in the patent the pressing is to be done at a temperature below 230° F. It is also to be done in the absence of caustic. Since this pressing only removes about half of the oil content, the remaining half of the oil left in the pressed cake can then be solvent extracted with hexane. This hexane extracted portion is then distilled to remove the solvent and the solvent-free oil fraction obtained has the following composition.
- Linolenic acid cis-cis - - - 50%
- Linoleic acid cis-cis - - - 15%
- Oleic acid - - - 22%
- Saturated fatty acid - - - 12%
- Crude flax phosphatides - - - 0.5%

This solvent-free oil is then centrifuged to separate it into a refined oil fraction and a gum fraction which is rich in phosphatide materials.

In one method of producing the special oil composition for use in this invention, I use a fraction of the crude pressed flaxseed oil in which the phosphatides have been retained. Since the pressed oil fraction only has about 0.1%–0.2% phosphatides additional phosphatides are added from two sources. From the gum fraction of the solvent extracted flax oil three parts of this phosphatide rich material are added per 100 parts of the pressed oil. To further increase the amount of phosphatides present, additional soy phosphatide is added in an amount of approximately 3% by weight.

This soy phosphatide is obtained by first converting the soy beans into crude oil. This can be done by grinding the soy beans into a powder, extracting the powder with hexane. The liquid mixture is distilled to obtain a solvent-free oil. The oil can be centrifuged to separate it into a refined oil fraction and a gum fraction which is rich in phosphatide materials. The phosphatide material is a triglyceride in conjunction with two fatty acids and one phosphatide chain which includes one molecule of choline and one of inositol.

This crude soy phosphatide is added to the previously fortified crude flaxseed oil so that the total phosphatide content is 6%. The oil contains about 6 I.U. of Vitamin E per 15 grams of oil. To this oil about 18 I.U. of Vitamin E are added as mixed grain and soya tocopherols per 15 grams of oil to make the total about 24 I.U. per 15 grams of oil. The total Vitamin E activity can range from about 20 I.U. to 25 I.U.

These mixed tocopherols are made of tocopherols from grains and soybeans. They are obtained as by-products in the vegetable oil extraction industry because edible oils such as soya, corn, and cottonseed will not harden in hydrogenation unless a considerable portion of the tocopherols are removed. In refining these oils about half of the tocopherols are removed. They are refined and sold as mixed tocopherols and can be obtained from Distillation Products Company in Rochester, New York.

The mixed tocopherols contain alpha, beta and gamma tocopherols with the alpha tocopherol being the basis for the Vitamin E activity. The alpha tocopherol has three methyl groups while the beta and gamma tocopherols have only two methyl groups each. The alpha tocopherol is about one I.U. of Vitamin E activity per milligram and one gram contains about 1000 I.U. Since the beta and gamma tocopherols have less Vitamin E activity the amount of mixed tocopherols required will be greater to produce an equivalent amount of Vitamin E. As a result the mixed tocopherols contain about one I.U. of Vitamin E activity per two milligrams. Thus to obtain 18 I.U. it would be necessary to use about 36 milligrams of the mixed tocopherol for a fifteen gram portion of the oil and this amount to less than 1% by weight of the oil. The fortified oil is then reduced to deep freeze temperature of 0° F.

This oil when fed to one subject (FIG. 1) at a rate of 15 ml per day, reduced PAI in five days time from 55 to 20.

Figure 2:
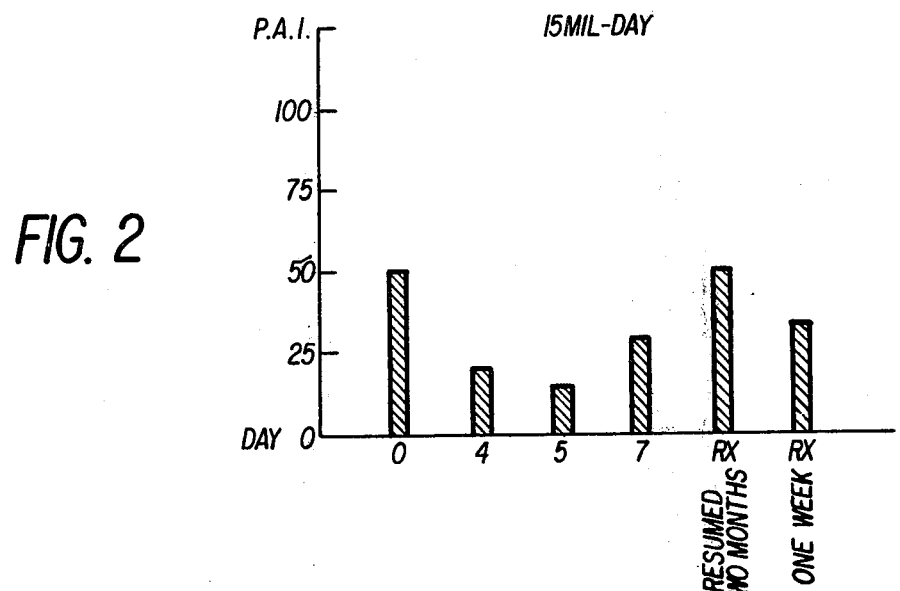

As I contemplate blending this oil with the other materials, I found it advisable to reduce iodine number from 190 to 170 so next I added to this oil 30% by weight crude hexane extracted soya oil. This mixture comprises: Linolenic acid cis-cis, 38%; Linoleic acid cis-cis, 30%; Oleic acid, 20%; and Saturated fatty acid, 9%; Crude soya phosphatide, 2.6%; and Crude flax phosphatides, 0.4% (70% flaxseed oil, 30% soya oil with 3% crude phosphatides) and 18 I.U. of Vitamin E as mixed soya tocopherol per 15 grams of oil. The mixture was given to fifteen subjects and the PAI was again reduced in five to ten days time from values of 50–70 to 20–35. When the subjects were deprived of the oil, gains in reduction were immediately lost as shown in FIG. 2.

Figure 3:
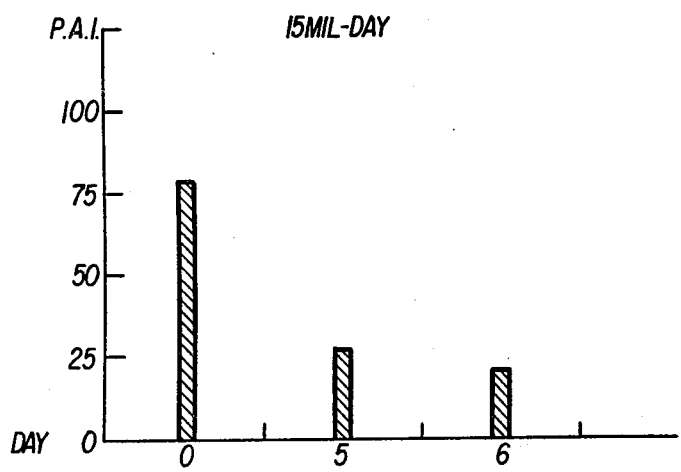

While subjects do not respond to the same degree to the regimen of 15 ml per day, an exceptional response in PAI reductions is that shown in FIGS. 3 and 4, where the subject received 15 ml per day of the product described herewith. A composite of a group of 15 treated males is shown in FIG. 5 in comparison with nontreated males who are coronary prone and untreated females.

This PAI reducing activity of the described composition was essentially the same as the flaxseed oil without the addition of crude soya oil. In other words my findings indicate the interchangeability of linolenic and linoleic acids.

Next, I tested refined flaxseed oil.

This refined flaxseed oil was from the same supply as used by Owren and on which he reported no reduction in PAI. I likewise found no reduction in PAI with this refined flaxseed. My findings insofar as the PAI reducing activity of oil made in accordance with my U.S. Pat. No. 3,163,545, as stated above are contrary to that reported by Owren who reported that there could be no reduction in PAI, with crude or refined flaxseed oil in his analysis of Oct. 23, 1965. I am unable to explain why my results are in the complete variance with the results of skilled researches in the past but I have reasons to believe that such variance has occurred because previous researchers allowed the phosphatide to settle and become separated from the main quantity of oil, I have found it absolutely essential that the crude phosphatide be distributed throughout the oil and in fact, I find it necessary to enrich the phosphatide content to about 6% of the total quantity of the mixture for the best results. Notwithstanding my departure from the prior art, I am able to duplicate my results consistently, even though they proceed directly contrary to reports in the prior art. I have found with test subjects (FIG. 2) that when my comparison was withheld after a course of treatment, the PAI of the subject reverted to excessive values within a few weeks to the preingesting level of 50–70 (FIG. 2). This indicates the need of continual ingesting. Thus we have a case when several corroborating sources are in agreement that flaxseed oil will not reduce PAI, whereas oil made in accordance with my formula (U.S. Pat. No. 3,163,545) together with the other ingredients does reduce PAI in a short time and by drastic amounts. These results suggest the presence of a beneficial material or materials in the crude phosphatides in my oil which must however be used together with linolenic or linoleic acid or both to cause a reduction of PAI.

In addition to the linolenic acid, linoleic acid, oleic acid, saturated fatty acids and the phosphatide, there are also small amounts of materials entrapped in the phosphatide such as B vitamins which include B6, niacin, and inositol; choline, and crude tannins. While it is not known which of these entrapped materials is the desired or necessary "X" factor, it is known that by following the teaching of this invention a subject will achieve PAI reduction and such lowering will require one or more X factors in combination with the linolenic or linoleic acids. There is some evidence also to indicate that Vitamin E, while not sufficient by itself to reduce PAI, may be a factor which accounts for the PAI reduction when used in conjunction with linolenic or linoleic acid and another substance or substances. It is also believed that the tocopherols added to provide the Vitamin E serve as a "preventor" since they prevent unsaturated fatty acids from being converted to harmful peroxide fats. For example, the beta and gamma tocopherols prevent peroxidation in the gut while alpha tocopherol which provides the Vitamin E action prevents peroxidation of unsaturated fatty acids in the blood. These peroxide fats are carcinogenic and can give rise to ulcers and cause hemolysis which is the destruction of red cells. It should be appreciated the results applied to the experimentation are so unexpected that skilled researchers are at a loss to explain on a theoretical and compositional level why I have achieved the results reported herein.

It would seem that the linolenic or linoleic acid content of the fat or oil is not greatly important insofar as PAI reduction is concerned. What is important is total amount of linolenic or linoleic acid digested per day along with the active supplemented material needed to activate it.

As a result of my foregoing discoveries concerning the completely contraindicated test results, I have found that a composition effective for reducing platelet adhesiveness index, may be comprised of:

EXAMPLE 1

Vegetable oil, manufactured in accordance with U.S. Pat. No. 3,163,545, from flaxseed oil has the following composition:

| | | |
|---|---|---|
| Linolenic acid cis-cis | 50 | % |
| Linoleic acid cis-cis | 15 | % |
| Oleic acid | 22.8 | % |
| Saturated fatty acids | 12 | % |
| Crude flax phosphatides | 0.2 | % |
| | 100.0 | % |
| To this is added | | |
| Crude soya phosphatides | 3 | % |
| Crude flax phosphatides | 3 | % |
| Mixed soya tocopherols added in the amount of 18 I.U. Vitamin E activity as mixed grain and soya tocopherols per 15 grams of oil. | | |

I further anticipate that a vegetable oil to reduce PAI containing a minimum of 6% linolenic acid cis-cis may be made in accord with U.S. Pat. No. 3,163,545 with any of the following supplemental oils: flax, rose, walnut, millet, sunflower, corn, safflower, cotton, peanut, rice, olive, wheat or soya containing in the order of a minimum of 2% crude phosphatides in which case the phosphatides can be from any of the above mentioned oils.

In each of the embodiments of the invention, the net effect is to produce a reduction in platelet adhesiveness which may be directly related to the incidence of coronary thrombosis, and by reason of a substantial reduction in platelet adhesiveness, the occurrence of coronary thrombosis may be suppressed. In consequence to these results, I have provided the possibility of dietary anti-coagulant prophylactic therapy. It is possible to incorporate the reduced iodine number material, i.e., 70%-30% mix material, into a sweet roll, such as a danish pastry, or the like, and the oil ingested is part of the sweet roll composition. In this way I avoid any of the taste factors associated with the oils used in the present invention.

The specific mechanics of how my discoveries have accomplished the results are not completely understood, nor do I advance any theories as to how the effect is achieved from a physiological standpoint. Nevertheless, my discoveries are based upon precise observations and these observations and results can be duplicated from one subject to the next and although individual effects can vary, it is found that the response is uniform insofar as PAI reduction is concerned.

It is expected that individual adjustments are necessary from one individual to the next in order to achieve a preferred PAI reduction and such adjustments are well within the skill of the art to make. The presently preferred dosage is 15 ml of the oil per day as shown in FIG. 1. Although lower amounts could be used it is suggested that at least 70% of this 15 ml per day be employed.

The composition can be given to both male and females. In general women not on the birth control pill are relatively free from the consequences of intravascular thrombosis until after the menopause. However women over 40 years of age on the birth control pill and post menopause women would be proper subjects for the present treatment.

It has been further found that when the phosphatide enriched material is allowed to stand and the phosphatides settle so that the oil ingested is impoverished of phosphatides, then PAI reduction does not occur. Accordingly, it is necessary to provide enough mechanical stirring in order that the phosphatide will be distributed evenly throughout the oil, otherwise the results of my invention are not achieved. The crude phosphatide-oil combination must be blended so that the percent by weight of the phosphatide is not substantially less than 2% by weight of the mixture and preferred results are obtained when the crude phosphatide is approximately 6% by weight. These limitations are not expressed however, to imply any criticality of the upper limit of the crude phosphatide, the result being that 6% concentration is adequate and no further value being notably present upon increase in the percent of crude phosphatide about this amount. However, when the crude phosphatide does fall appreciably below the 2% concentration, then the benefits of the material are diminished at a significant value in PAI reduction. This described material can be used in a process for producing platelet adhesiveness index by either combining the oil with a food product which can then be baked or made into any other flavorful product and such procedure has substantial advantages in that the oil loses its inherent disagreeable taste and aroma. However, if the oil is combined with a food product which requires heating, then any other material which is combined with it must be selected with a view in mind to protecting the inherent antioxident characteristic of the enriched oil.

The oil may also be ingested in the form of a pill or liquid.

Although the present invention has been illustrated and described in conjunction with a few selected example embodiments, it will be understood that these are illustrative of the invention and are by no means restrictive thereof. It is reasonably to be expected that those skilled in the art can make revisions and adaptations of the present invention, as for example, in pill form or liquid form, and it is intended that such revisions and adaptations of the present invention will be incorporated within the scope of the following claims as equivalents of the invention.

What is claimed is:

1. A process for reducing platelet adhesiveness in flowing human blood which comprises orally administering to humans a platelet adhesiveness reducing amount of an edible oil obtained by
   pressing flaxseeds at a temperature below about 230° F and in the absence of caustic to obtain a first major portion of flaxseed oil;
   adding approximately 3% by weight, based on the weight of the flaxseed oil, of soy phosphatide obtained by centrifuging an oil obtained from soy beans and separating the soy phosphatide from the centrifuged oil;
   adding approximately 3% by weight, based on the weight of the flaxseed oil, of a flax phosphatide obtained by centrifuging an oil obtained from flaxseeds and separating the flax phosphatide from the centrifuged oil; and
   adding mixed grain and soya tocopherols in an amount of less than 1% by weight based on the weight of the flaxseed oil.

2. A process according to claim 1, wherein said soy phosphatide is obtained by grinding soy beans into a powder, extracting the powder with hexane to form a liquid mixture, distilling said liquid mixture to obtain a hexane-free oil, centrifuging said hexane-free oil to obtain the soy phosphatide which is dried for use in forming the edible oil.

3. A process according to claim 1, wherein said flax phosphatide is obtained by pressing flaxseeds to remove part of the flaxseed oil and leaving a pressed flaxseed cake, extracting said flaxseed cake with hexane to form a liquid mixture, distilling said liquid mixture to obtain a hexane-free oil, centrifuging said hexane-free oil to obtain the flax phosphatide which is dried for use in forming the edible oil.

4. A process according to claim 1, wherein said tocopherols are added in an amount corresponding to about 18 I.U. of Vitamin E per 15 ml of oil.

5. A process according to claim 1, wherein said edible oil is administered admixed with a palatable foodstuff.

* * * * *